US00PP19831P3

(12) United States Plant Patent
Anderson

(10) Patent No.: US PP19,831 P3
(45) Date of Patent: Mar. 17, 2009

(54) ***CHRYSANTHEMUM* PLANT NAMED '00-100-382'**

(50) Latin Name: *Chrysanthemum×hybrida*
Varietal Denomination: 00-100-382

(75) Inventor: Neil O. Anderson, St. Paul, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 84 days.

(21) Appl. No.: 11/803,912

(22) Filed: May 16, 2007

(65) Prior Publication Data

US 2007/0271649 P1 Nov. 22, 2007

Related U.S. Application Data

(60) Provisional application No. 60/800,972, filed on May 17, 2006.

(51) Int. Cl.
*A01H 5/00* (2006.01)

(52) U.S. Cl. ..... Plt./286

(58) Field of Classification Search ..... Plt./286, Plt./284
See application file for complete search history.

(56) References Cited

PUBLICATIONS

"Top Performing Annuals and Perennials for 2006," Andersen et al., University of Minnesota, dept. of Horticultural Science. (5 pages total).*
"New Flowers Bred a the U. Herbaceous Perennial Breeding Program". ( 9 pages total).*
Brummit, R.K.; "The Garden," "*Chrysanthemum* once again," Sep. 1997; pps. 662–663. ( 2 pages total).*

* cited by examiner

*Primary Examiner*—Annette H Para
*Assistant Examiner*—S. B. McCormick Ewoldt
(74) *Attorney, Agent, or Firm*—Penny J. Aguirre

(57) ABSTRACT

A new cultivar of *chrysanthemum*, '00-100-382', characterized by it's early blooming habit with frost tolerant single to duplex daisy-type inflorescences with dark purple ray florets and gold disk florets, its vigorous shrub-like growth habit after two years of growth, its tight cushion plant form attained without pinching, and its good garden performance and winter hardiness.

2 Drawing Sheets

STATEMENT REGARDING FEDERALLY SPONSORED RESEARCH

This invention was made with government support under MIN-21-50 and MIN-21-52 awarded by the U.S. Dept. of Agriculture. The government has certain rights in the invention.

Botanical classification *Chrysanthemum×hybrida.*

Variety denomination: '00-100-382'.

BACKGROUND OF THE INVENTION

The present invention relates to a new and distinct-cultivar of garden *chrysanthemum* plant, botanically known as *Chrysanthemum×hybrida* '00-100-382' and will be referred to hereinafter by its cultivar name, '00-100-382'. The new cultivar is commercially known as a garden-type *chrysanthemum.*

'00-100-382' was derived from an on going controlled breeding program that focuses on obtaining new cultivars of garden *chrysanthemums* in a range of flower colors that exhibit superior winter hardiness for northern climates, a large shrub-like habit in successive growth years that, and a tight cushion plant habit without the need for pruning or pinching. The breeding originally commenced with crosses utilizing *Chrysanthemum weyrichii* 'Pink Bomb' (not patented) and various unpatented cultivars of *Chrysanthemum×grandiflora.*

The new cultivar, '00-100-382', was created with a series of crosses and selections made over a period of years between 1986 and 2000 utilizing proprietary selections. '00-100-382' ultimately originated from a cross-pollination made in 2000 of proprietary seedling designated as '89-98-13' (not patented) as the female parent and the proprietary seedling designated as '00-100-352' (not patented) as the male parent. The new *chrysanthemum* was selected as a single plant within the progeny of the stated cross in 2000 by the inventor in St. Paul, Minn. '00-100-382' was selected as unique for its single to duplex, daisy-type inflorescences with dark purple ray florets and gold disk florets combined with the characteristics that fit the objectives of the breeding program.

Asexual reproduction of the new cultivar was first accomplished via stem cuttings in St. Paul, Minn. in 2001. The characteristics of this cultivar have been determined to be stable and are reproduced true to type in successive generations.

Comparisons: '89-98-13' (female parent) has semi-double inflorescences with ray florets that are deeper purple in color than '00-100-382', '00-100-352' (male parent) has single inflorescences with ray florets that are white in color. 'Erin' (U.S. Plant Patent Pending) is a 7 wk variety (mid season) whereas '00-100-382' is an early season (6 wk response group), indicating that it will flower ~1 wk earlier than 'Erin'. Plant habit of 'Erin' and '00-100-382' are the same, i.e. cushion or ball-shaped, but '00-100-382' differs from 'Erin' by being winter hardy, surviving as a perennial in northern climates. Likewise, in the 2nd and successive years of growth, the cushion habit remains unchanged in '00-100-382' but the plant size (height, width) increases to form a shrub habit and supersedes the plant size of 'Erin'.

SUMMARY OF THE INVENTION

The following traits have been repeatedly observed and are determined to be the characteristics of the new cultivar of *chrysanthemum*. These attributes in combination distinguish '00-100-382' as unique from and all other varieties of *chrysanthemum* known to the inventor.

1. '00-100-382' is early blooming and exhibits single to duplex daisy-type inflorescences with dark purple ray florets and gold disk florets.
2. '00-100-382' attains a large shrub-like habit in the second and successive years of growth attaining about 30 to 46 cm in height the first year and about 91 to 122 cm in height and 122 cm in width in the second year.
3. '00-100-382' forms a tight cushion plant form without the need for pinching or pruning.
4. '00-100-382' exhibits extreme hybrid vigor.
5. '00-100-382' exhibits a massive floral display in its second and subsequent years after planting.
6. '00-100-382' is a winter hardy shrub *chrysanthemum* with hardiness to U.S.D.A. Zone 3.
7. The inflorescences of '00-100-382' are frost tolerant.

BRIEF DESCRIPTION OF THE DRAWINGS

The accompanying colored photographs illustrate the overall appearance and distinct characteristics of the new *chrysanthemum*. The photographs were taken of plants grown for two years under field conditions in Waseca, Minn.

Figure 1:
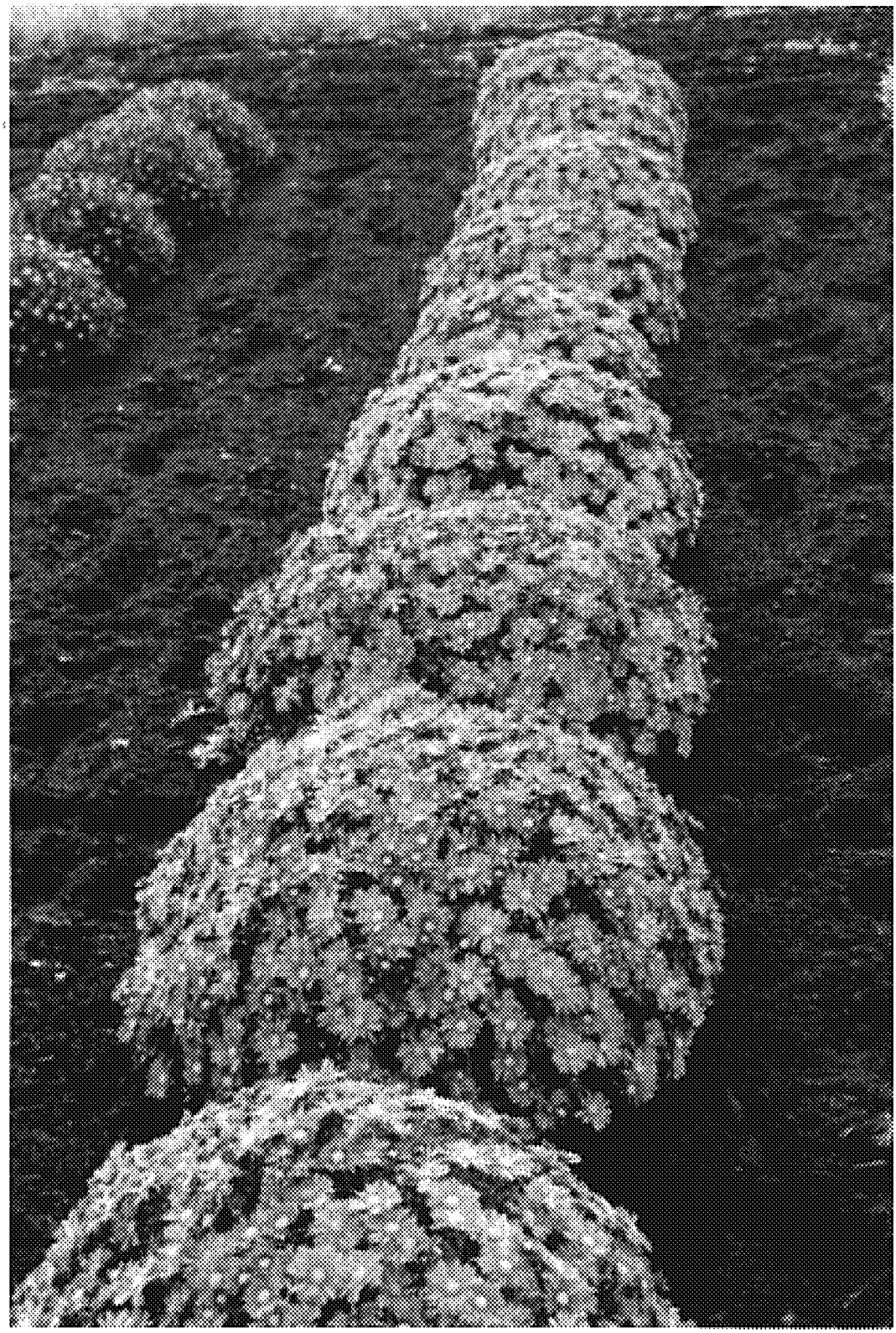
FIG. 1 is a photograph of a row of '00-100-382' plants after two years of growth.
Figure 2:
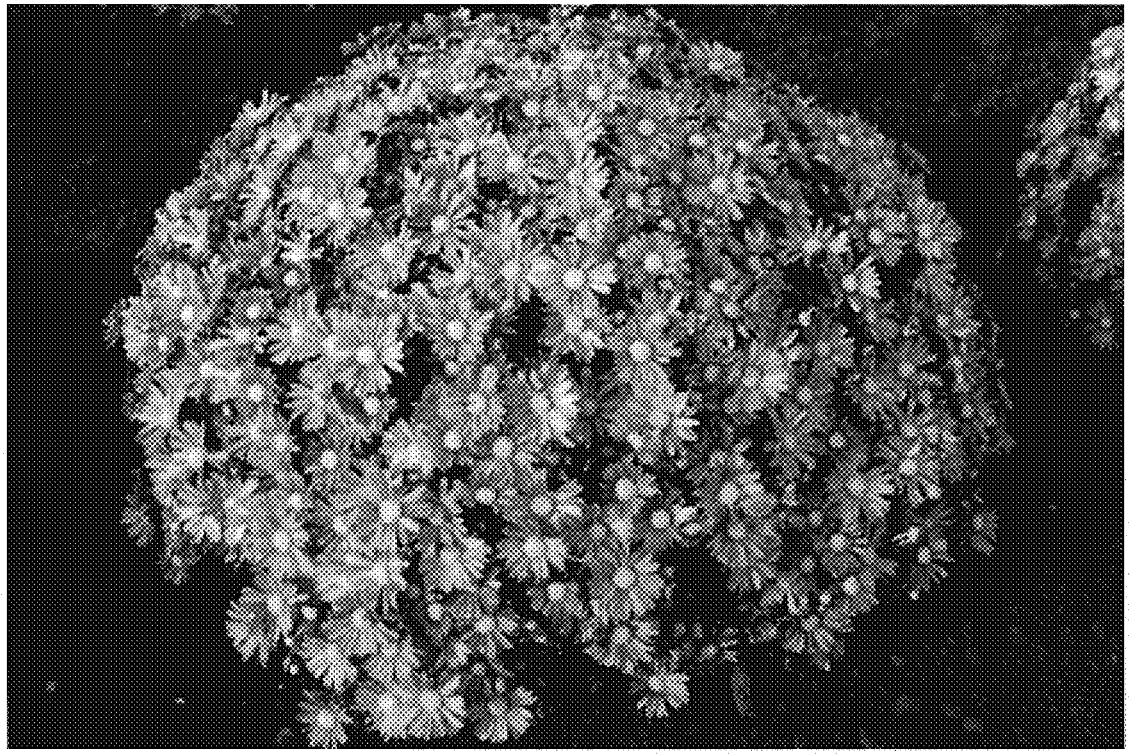
FIG. 2 is a photograph of a single plant of '00-100-382' after two years of growth.
Figure 3:
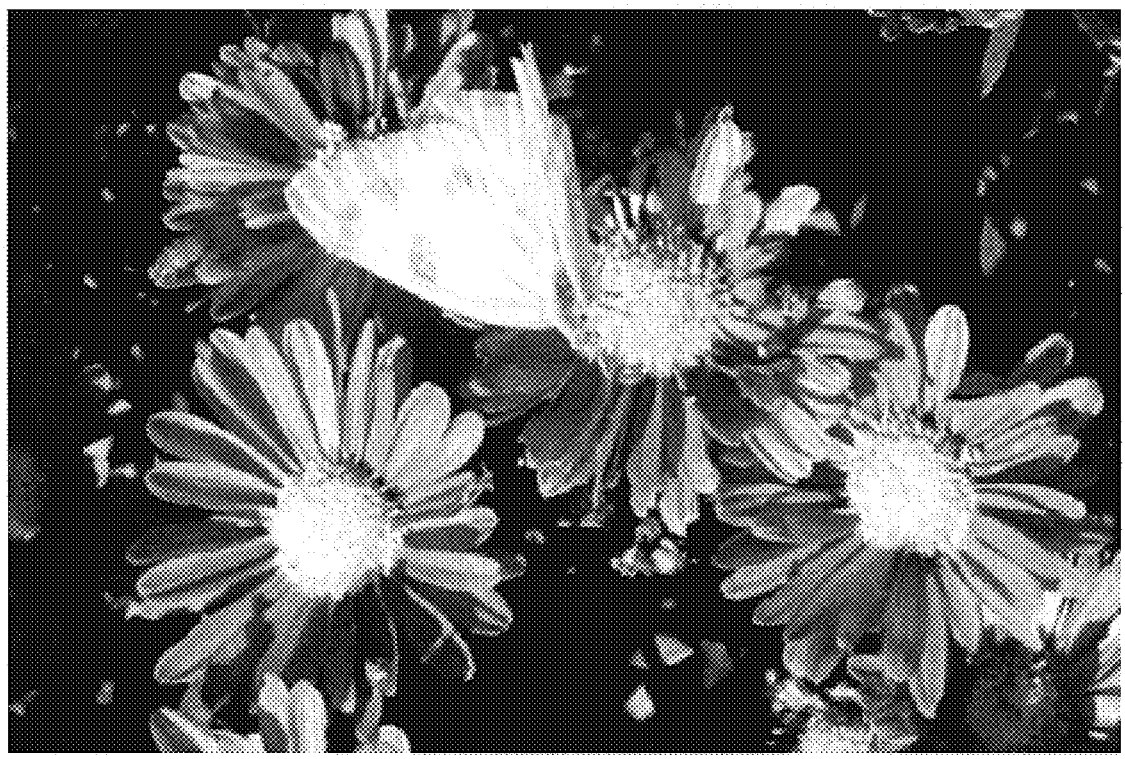

The photograph in FIG. 3 provides a close-up view of the flowers of '00-100-382'.

The colors in the photographs are as close as possible with the photographic and printing technology utilized. The color values cited in the detailed botanical description accurately describe the colors of the new *chrysanthemum*.

DETAILED BOTANICAL DESCRIPTION

The following is a detailed description of the new cultivar as grown outdoors under natural lighting in a trial bed in Waseca, Minn. and observed over a period of two years. The detailed botanical data was collected from one and two year-old plants between 1:00 and 5:00 p.m. on Sep. 27, 2005. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General Description:

*Blooming season.*—Early season, flowers as early as week 32 in Grand Rapids, Minn. (USDA Z3) and continues through early October (wk 40) until a killing freeze has occurred. In Waseca, Minn. (USDA Z4), '00-100-382' flowers as early as wk 30, extending through wk 40.

*Plant habit.*—Herbaceous perennial, mounded habit, produces a cushion form in the first year of growth, attains a larger shrub-like habit in the second and subsequent years with a tight cushion plant form.

*Height and spread.*—Reaches about 40 cm in height and 74.5 cm in width in the first year and about 49 cm in height and 116 cm in width in the second and subsequent years.

*Hardiness.*—U.S.D.A. Zone 3.

*Diseases resistance.*—No susceptibility or resistance to diseases common to *chrysanthemum* has been observed.

*Root description.*—Fibrous.

Growth and Propagation:

*Propagation.*—Stem cuttings.

*Time to root initiation.*—About 1 week.

*Crop maintenance.*—No pinching or pruning is required to achieve the cushion plant habit and abundant bloom.

*Growth rate.*—Vigorous.

Stem Description:

*Stem color.*—First year growth 144A with some hairy faint striations of 177B, second year growth 144B with some hairy faint striations of 177B.

*Lateral branch length.*—Average of 29 cm.

*Lateral branch diameter.*—Average of 2.5 mm.

*Quantity of lateral branches.*—About 52 per plant in second year, average of 6 lateral branches produced per stem if apical meristem is removed (pinched).

*Internode length.*—Average of 1.3 cm.

Foliage Description:

*Leaf division.*—Simple.

*Leaf shape.*—Blade is ovate to obovate with narrow region extending towards base.

*Leaf base.*—Cuneate.

*Leaf apex.*—Acute.

*Leaf margin.*—Incised (mulberry-like incisions) to 0.5 cm deep.

*Leaf venation.*—Upper surface 145C, lower surface 144D.

*Leaf attachment.*—Sessile.

*Leaf arrangement.*—Alternate.

*Leaf number.*—Average of 23 per lateral branch.

*Leaf surface.*—Glabrous on upper surface, slightly pubescent on lower surface.

*Leaf color.*—Young foliage; upper surface 137A, lower surface 137B, mature foliage; upper surface 137B, lower surfaces 146B.

*Leaf size (fully expanded).*—Average of 5.2 cm in length and 2.4 cm in width.

*Fragrance of foliage.*—Fragrant if bruised.

Flower Description:

General Description:

*Inflorescence type.*—Composite.

*Flowering response.*—6 weeks of short days.

*Lastingness of inflorescence.*—Temperature dependent, under normal field conditions during the fall, flowers typically last about 2 to 4 weeks, although flowering of the entire plant extends from 7 to 10 weeks.

*Fragrance.*—None.

*Quantity of inflorescences.*—About 6,860 flowers per plant in second year.

*Inflorescence buds.*—About 7.4 mm in depth and 9.4 mm in diameter, globose in shape, color 144D with stripes on phyllaries 137C.

*Inflorescence size.*—About 1.3 cm in depth and 3.9 cm in diameter, diameter of disk about 1 cm.

*Peduncle.*—Strong, held at an angle of 55° to stem, texture is hirsute, first peduncle is an average of 6.5 cm in length and fourth peduncle is an average of about 7.7 cm in length, color is 138B with hairy coating of 138D.

*Involucral bracts (phyllaries).*—Crenulate in appearance, 137B in color, about 2 to 5 mm in length, less than 1 mm in width, glabrous in texture.

Ray Florets: (capitulate)

*Number.*—Average of 54 arranged in a single or double whorl (duplex).

*Shape.*—Spatulate.

*Aspect.*—Upright at an angle of 45°.

*Size.*—Average of 1.8 cm in length and 4.4 mm width.

*Petal apex.*—Retuse.

*Petal base.*—Cuneate.

*Petal margins.*—Entire.

*Petal texture.*—Glabrous on upper and lower surfaces.

*Petal color.*—Opening; Upper surface 75A with markings of N79C, lower surface 75B with markings of N79D, fully open; upper surface 70A, lower surface 84B, fading; upper surface 75A, lower surface 75B.

Disk Florets (perfect):

*Quantity.*—Average of 200.

*Shape.*—Tubular.

*Size.*—About 4 mm in length and 1 mm in width when mature.

*Color.*—Immature and mature 1C with a tip of 13B.

Reproductive Organs:

*Presence.*—Disk flowers are perfect, ray flowers are carpellate.

*Gynoecium.*—1 Pistil per disk and ray floret, style color 13C.

*Androecium.*—1 stamen per disk floret, fused into tube surrounding style, anther color 13B, pollen little in quantity, and 12A in color.

*Fruit and seed.*—About 254 ovules per floret. Fruit is an achene with a single seed attached to the ovary wall. Seed lacks pappus, have a compressed oval shape with pointed ends, are about 2 to 5 mm in length and 1 to 2 mm in width with a ridged texture and 200D in color.

I claim:

1. A new and distinct variety of *chrysanthemum* plant designated '00-100-382' as described and illustrated herein.

* * * * *